(12) United States Patent
Rafter et al.

(10) Patent No.: US 6,740,039 B1
(45) Date of Patent: May 25, 2004

(54) METHODS AND APPARATUS FOR DISPLAYING INFORMATION RELATING TO DELIVERY AND ACTIVATION OF A THERAPEUTIC AGENT USING ULTRASOUND ENERGY

(75) Inventors: Patrick G Rafter, Windham, NH (US); Susan E Beiter, Ayer, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/572,268

(22) Filed: May 17, 2000

Related U.S. Application Data

(60) Provisional application No. 60/150,045, filed on Aug. 20, 1999.

(51) Int. Cl.$^7$ .................................................. A61B 8/00
(52) U.S. Cl. ............................................ 600/439; 601/2
(58) Field of Search .............................. 600/439; 601/2, 601/3; 607/97

(56) References Cited

U.S. PATENT DOCUMENTS

| | | | | |
|---|---|---|---|---|
| 5,190,766 A | * | 3/1993 | Ishihara | 424/489 |
| 5,255,683 A | | 10/1993 | Monaghan | 128/662.02 |
| 5,456,257 A | | 10/1995 | Johnson et al. | 128/662.02 |
| 5,490,840 A | * | 2/1996 | Uzgiris et al. | 604/22 |

(List continued on next page.)

FOREIGN PATENT DOCUMENTS

| | | |
|---|---|---|
| EP | 0851241 A2 | 7/1998 |
| WO | WO 96/22111 | 7/1996 |
| WO | WO 98/48783 | 11/1998 |
| WO | WO 99/39697 | 8/1999 |
| WO | WO 00/12062 | 3/2000 |

OTHER PUBLICATIONS

P. Rafter, "Harmonic Power Doppler Technology", 4th Heart Centre Sym. on Ultrasound Contrast Imaging, Jan. 21–22, 1999, 2 pages.

J. Cheirif, "HP Acoustic Densitometry: A New Echocardiographic Method for the On–Line Quantitative Assess ment of Contrast Echocardiograms", Application Note, 1996, 4 pages.

D. L. Miller, "Ultrasonic Detection of Resonant Cavitation Bubbles in a Flow Tube by their Second Harmonic Emissions", Ultrasonics, Sep. 1981, pp. 217–224.

*Primary Examiner*—Mary Beth Jones
*Assistant Examiner*—Ruby Jain
(74) *Attorney, Agent, or Firm*—John Vodopia

(57) ABSTRACT

A therapeutic agent is incorporated into microbubbles of a contrast agent, and the microbubbles containing the therapeutic agent are delivered to a region of interest in a patient. An ultrasound image of the region of interest is generated by an ultrasound imaging system, and ultrasound energy for destroying the microbubbles of the contrast agent is transmitted to the region of interest. Parameter data that is representative of activation of the therapeutic agent in the region of interest is acquired, and a parameter display is generated. One or more parameters of the ultrasound energy applied to the region of interest for activating the therapeutic agent may be adjusted, either manually based on the parameter display or automatically based on acquired parameter data. In one embodiment, the parameter display is indicative of a parameter associated with the ultrasound energy transmitted to the region of interest. In another embodiment, the parameter data is acquired by detecting destruction of microbubbles of the contrast agent.

32 Claims, 5 Drawing Sheets

U.S. PATENT DOCUMENTS

| | | | |
|---|---|---|---|
| 5,558,092 A | 9/1996 | Unger et al. | 128/660.03 |
| 5,577,505 A | 11/1996 | Brock-Fisher et al. | 128/662.02 |
| 5,657,760 A * | 8/1997 | Ying et al. | 600/439 |
| 5,675,554 A | 10/1997 | Cole et al. | 367/138 |
| 5,706,819 A | 1/1998 | Hwang et al. | 128/662.02 |
| 5,740,128 A | 4/1998 | Hossack et al. | 367/138 |
| 5,833,613 A | 11/1998 | Averkiou et al. | 600/440 |
| 5,984,881 A * | 11/1999 | Ishibashi et al. | 601/2 |
| 6,039,967 A | 3/2000 | Ottoboni et al. | 424/426 |
| 6,086,535 A * | 7/2000 | Ishibashi et al. | 600/439 |
| 6,224,553 B1 * | 5/2001 | Nevo | 600/437 |
| 6,224,554 B1 * | 5/2001 | Tickner et al. | 600/438 |
| 6,340,348 B1 * | 1/2002 | Krishnan et al. | 600/447 |

* cited by examiner

METHODS AND APPARATUS FOR DISPLAYING INFORMATION RELATING TO DELIVERY AND ACTIVATION OF A THERAPEUTIC AGENT USING ULTRASOUND ENERGY

This application claims priority under 35 U.S.C.§119(e) from U.S. provisional application No. 60/150,045 filed Aug. 20, 1999.

FIELD OF THE INVENTION

This invention relates to delivery of a therapeutic agent to a region of interest using a contrast agent and activation of the therapeutic agent using ultrasound energy and, more particularly, to methods and apparatus for displaying information relating to delivery and activation of the therapeutic agent.

BACKGROUND OF THE INVENTION

Ultrasound imaging is widely used in diagnostic medical applications to non-invasively observe structures within the human body, such as cardiac structures, the vascular system, the fetus, the uterus, the abdominal organs and the eye. In a typical imaging system, short bursts of ultrasound energy are directed into a patient's body with a handheld transducer. The returning reflected energy is received by the same transducer, and signals representing the reflected energy are processed and formatted into a video image of the target region. Phased-array scanning techniques are commonly used.

Current trends in research involve investigations of non-linear responses to, ultrasound energy. For example, some contrast agents have been found to provide a harmonic response to ultrasound energy. This response can be used to provide increased diagnostic information about the tissue in a region of interest. Many contrast agents demonstrate tissue perfusion when administered through intravenous injection. The contrast agents are often configured as microbubbles that comprise a shell which acts to contain an internal gas or other contrast enhancing agent. For instance, perfluorocarbon-exposed sonicated dextrose albumin microbubbles have been employed to improve the contrast of ultrasound images. Typically, these microbubbles can be destroyed if sufficiently high levels of ultrasonic energy are applied. Diagnostic ultrasound imaging with contrast agents is disclosed in U.S. Pat. Nos. 5,833,613 issued Nov. 10, 1998 to Averkiou et al; U.S. Pat. No. 5,740,128 issued Apr. 14, 1998 to Hossack et al; U.S. Pat. No. 5,255,683 issued Oct. 26, 1993 to Monaghan; U.S. Pat. No. 5,456,257 issued Oct. 10, 1995 to Johnson et al; U.S. Pat. No. 5,577,505 issued Nov. 26, 1996 to BrockFisher et al; and U.S. Pat. No. 5,706,819 issued Jan. 13, 1998 to Hwang et al, and in European Patent Application No. EP 0 851 241 published Jul. 1, 1998.

Ultrasound systems may also be utilized in connection with the targeted delivery of a therapeutic agent, such as a drug or a gene, to a region of interest. The therapeutic agent is encapsulated in or is otherwise attached to microbubbles of a contrast agent. The contrast agent containing the therapeutic agent is administered to a region of interest in a patient, and ultrasound energy is applied to the region of interest, causing destruction of the microbubbles, and release, or activation, of the therapeutic agent. This technique is disclosed, for example, in U.S. Pat. No. 5,558,092 issued Sep. 24, 1996 to Unger et al.

The delivery and activation of a therapeutic agent in this manner must be controlled in order to ensure proper dosage. Accordingly, there is a need for measurement and display techniques which facilitate control of the process.

SUMMARY OF THE INVENTION

According to a first aspect of the invention, a method is provided for administering a therapeutic agent, such as a drug or a gene, to a patient. The method comprises the steps of delivering a therapeutic agent to a region of interest, generating an ultrasound image of the region of interest, transmitting ultrasound energy to the region of interest for activating the therapeutic agent, and generating a parameter display that is indicative of activation of the therapeutic agent in the region of interest.

Preferably, the therapeutic agent is incorporated into microbubbles of a contrast agent, and the microbubbles containing the therapeutic agent are delivered to the region of interest. The transmitted ultrasound energy activates the therapeutic agent by destroying the microbubbles of the contrast agent and releasing the therapeutic agent.

The method may further include the step of adjusting one or more parameters of the ultrasound energy transmitted to the region of interest. The parameters of the transmitted ultrasound energy may be adjusted manually based on the parameter display or may be adjusted automatically based on acquired parameter data, such as a measurement of microbubble destruction in the region of interest. The parameter display thus provides feedback for control of the activation process.

In one approach, the parameter display may represent a parameter, such as ultrasound transmit power, ultrasound transmit frequency, ultrasound pressure or ultrasound mechanical index, of the ultrasound energy applied to the region of interest. In another approach, the parameter display may be generated by detecting microbubble destruction, and generating a display that is indicative of microbubble destruction in the region of interest.

In a first embodiment, the parameter display may comprise a colorized display. In one example, specified colors are indicative of cumulative dose of the therapeutic agent delivered to the region of interest. In another example, specified colors are indicative of parameter values or ranges of values associated with activating the therapeutic agent. In a second embodiment, the parameter display may comprise a graphical representation of a parameter that is indicative of activation of the therapeutic agent as a function of time or a spatial parameter. For example, the graphical representation may comprise a graph of cumulative dose of the therapeutic agent as a function of time. In a third embodiment, the parameter display may comprise an area display that overlays the ultrasound image and is indicative of the spatial distribution of a parameter. For example, the area display may show contours of constant value of a parameter.

According to another aspect of the invention, apparatus is provided for facilitating administration of a therapeutic agent to a patient. The therapeutic agent is incorporated into microbubbles of a contrast agent and is delivered with the contrast agent to a region of interest in the patient. The apparatus comprises means for generating an ultrasound image of the region of interest, means for transmitting ultrasound energy to the region of interest for destroying the microbubbles of the contrast agent, means for acquiring parameter data that is representative of destruction of the microbubbles of the contrast agent and means for generating a parameter display of the acquired parameter data. The parameter display is indicative of activation of the therapeutic agent in the region of interest.

According to a further aspect of the invention, a method is provided for administering a therapeutic agent to a patient. The method comprises the steps of delivering to a region of interest in a patient a therapeutic agent that is incorporated into microbubbles of a contrast agent, generating an ultrasound image of a region of interest, transmitting ultrasound energy to the region of interest for destroying the microbubbles of the contrast agent, acquiring parameter data that is indicative of activation of the therapeutic agent, and automatically adjusting one or more parameters of the ultrasound energy transmitted to the region of interest, based on the acquired parameter data.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
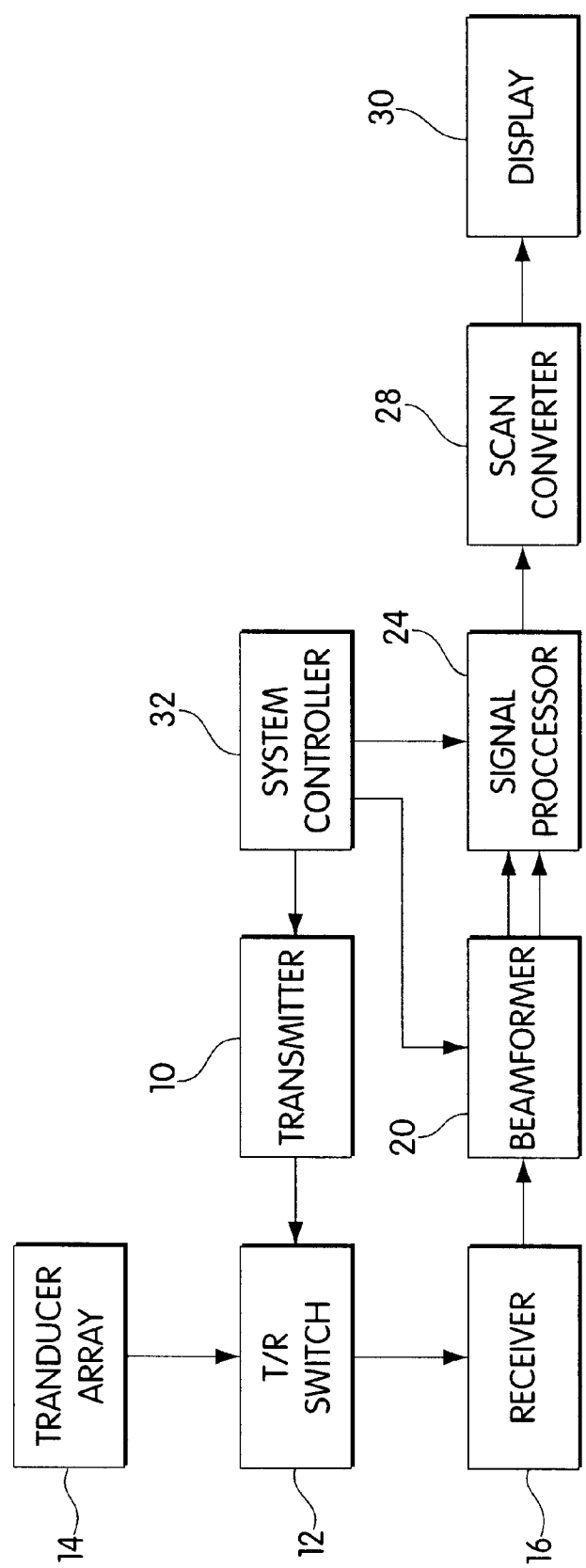
FIG. 1 is a block diagram of an example of an ultrasound system suitable for practice of the present invention.

A simplified block diagram of an ultrasound imaging system suitable for practice of the present invention is shown in FIG. 1. An ultrasound transmitter 10 is coupled through a transmit/receive (T/R) switch 12 to a transducer array 14. The transducer array 14 transmits ultrasound energy into a region being imaged and receives reflected ultrasound energy, or echoes, from various structures and organs within the patient's body. The transducer 14 includes an array of transducer elements. As known in the art, by appropriately delaying the pulses applied to each transducer element by transmitter 10, a focused ultrasound beam is transmitted along a desired transmit scan line.

The transducer array 14 is coupled through T/R switch 12 to an ultrasound receiver 16. Reflected ultrasound energy from a given point within a patient's body is received by the transducer elements at different times. The transducer elements convert the received ultrasound energy to received electrical signals which are amplified by receiver 16 and are supplied to a receive beamformer unit 20. The signals from each transducer element are individually delayed and then are summed by the beamformer unit 20 to provide a beamformer signal that represents the reflected ultrasound energy level along a given receive scan line. As known in the art, the delays applied to the received signals may be varied during reception of ultrasound energy to effect dynamic focusing.

The process is repeated for multiple scan lines to provide signals for generating an image of a region of interest in the patient's body. Typically, the scan pattern is a sector scan, wherein the scan lines originate at the center of the transducer array 14 and are directed at different angles. Linear, curvilinear and other scan patterns may also be utilized. The beamformer unit may be, for example, a digital beamformer of the type used in the HP Sonos 5500 ultrasound system manufactured and sold by Hewlett-Packard Company.

The beamformer signals are applied to a signal processor 24 which processes the beamformer signals for improved image quality. The output of signal processor 24 is supplied to a scan converter 28 which converts sector scan signals generated by beamformer unit 20 to conventional raster scan display signals. The output of scan converter 28 is supplied to a video display unit 30, which displays an image of the region of interest in the patient's body. A system controller 32 provides overall control of the system. The system controller 32 performs timing and control functions and typically includes a microprocessor and associated memory.

The exemplary ultrasound imaging system shown in FIG. 1 and described above may be used to implement a method for administering a therapeutic agent to a patient in accordance with the invention. As described above, ultrasound imaging systems may be utilized in connection with the targeted delivery of a therapeutic agent to a region of interest in a patient. As further described above, contrast agents may be configured as microbubbles which exhibit non-linear responses to ultrasound energy. A therapeutic agent may be attached to and carried by the microbubbles of a contrast agent. The therapeutic agent may be encapsulated within the microbubbles, may be incorporated into the shells of the microbubbles or may be attached to the outer surfaces of the microbubbles, or a combination of these techniques may be employed. The therapeutic agent may be a drug or a gene. In a preferred embodiment, the therapeutic agent is encapsulated within the microbubbles of the contrast agent.

The contrast agent containing the therapeutic agent may be delivered to a region of interest in a patient by intravenous injection. The therapeutic agent remains encapsulated within the microbubbles of the contrast agent until it is "activated". The therapeutic agent is activated by applying to the region of interest ultrasound energy of appropriate power level and frequency to destroy the microbubbles and thereby release the therapeutic agent. The activated therapeutic agent is then available to perform the intended therapeutic function in the region of interest.

Figure 2:
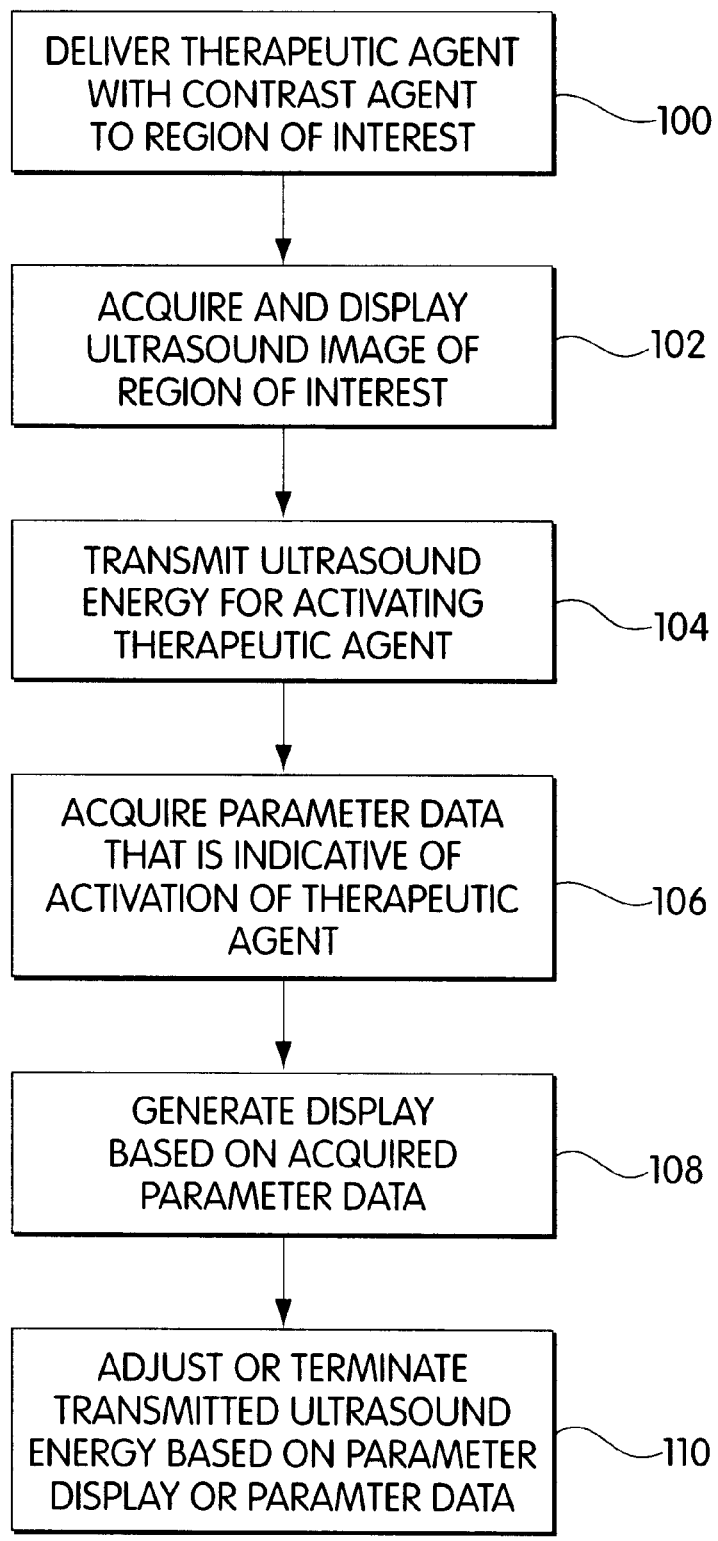
FIG. 2 is a flow chart showing an example of a method for administering a therapeutic agent in accordance with the invention.

A flow chart of an example of a process for administering a therapeutic agent in accordance with the invention is shown in FIG. 2. In step 100, the therapeutic agent is delivered with a contrast agent to a region of interest in the patient, as described above. In step 102, the ultrasound imaging system shown in FIG. 1 and described above is used to acquire and display an ultrasound image of the region of interest. The imaging system may be configured for harmonic imaging of the contrast agent, as known in the art. In particular, the receiver 16 and beamformer unit 20 may be configured for sensing ultrasound energy at a harmonic of the transmitted ultrasound frequency. The ultrasound image is displayed on video display unit 30. Delivery of the contrast agent containing the therapeutic agent may be confirmed by observing the ultrasound image.

As indicated above, the ultrasound energy destroys the microbubbles of the contrast agent and releases the therapeutic agent. Accordingly, the parameters of the ultrasound energy, including frequency, power level and beam pattern, are selected to release a desired dose of the therapeutic agent in the region of interest, and the ultrasound energy is applied to the region of interest in step 104. The ultrasound energy for activating the therapeutic agent may be transmitted by the system used for ultrasound imaging or by a separate ultrasound transmitter. In general, the ultrasound energy used for destruction of microbubbles may have lower frequency, higher power and a different beam pattern as compared with the ultrasound energy used for imaging. Thus, ultrasound energy for destruction of microbubbles and ultrasound energy for imaging may be transmitted at different times in an alternating sequence or other desired sequence. In some applications, the same transmitted ultrasound energy may be used for imaging and for microbubble destruction.

In step 106, parameter data that is indicative of activation of the therapeutic agent is acquired. The parameter data may be indicative of the dose of therapeutic agent and/or the spatial distribution of therapeutic agent in the region of interest. The parameter data may be derived from the parameters of the transmitted ultrasound energy used for activating the therapeutic agent, from the ultrasound energy received by the imaging system from the region of interest, or both. When the parameter data is derived form the ultrasound energy received from the region of interest, it may represent a measurement of microbubble destruction.

In step 108, the parameter data is used to generate a parameter display that is indicative of activation of the therapeutic agent. The parameter display may, indicate the spatial distribution of a parameter, such as transmit parameter or cumulative dose of the therapeutic agent, or may plot a parameter, such as cumulative dose, as a function of time. In one embodiment, the parameter display overlays the ultrasound image on the display screen of video display unit 30. For example, the spatial distribution of the measured parameter may be indicated as an overlay on the ultrasound image. In another embodiment, the parameter display and the ultrasound image may appear side by side or in any other desired arrangement on the display screen of video display unit 30. In yet another embodiment, the parameter display and the ultrasound image may appear on separate video display units. Examples of specific parameter data and parameter displays are described below.

The parameter display is indicative of activation of the therapeutic agent. Optimum delivery of the therapeutic agent requires a specified dose having a specified spatial distribution in the region of interest. The parameter display may indicate that the actual activation parameters differ from desired activation parameters. In step 110, application of ultrasound energy for activation of the therapeutic agent may be adjusted or terminated. For example, the frequency, power level and/or beam pattern of the transmitted ultrasound energy may be adjusted. Alternatively, application of ultrasound energy may be terminated when a desired dose of the therapeutic agent is indicated. The parameter display thus permits interactive control of the activation process. Steps 102–110 shown in FIG. 2 may be repeated until a desired result is achieved.

The control of the transmitted ultrasound energy may be manual or automatic. When the control is manual, the operator observes the parameter display and adjusts or terminates the transmitted ultrasound energy to produce a desired result. When the control is automatic, the system controller 32 may base adjustment or termination of the transmitted ultrasound energy on acquired parameter data, such as a measurement of microbubble destruction. For example, control of transmitted ultrasound energy may be based on average or cumulative microbubble destruction in a defined region of interest.

The present invention involves acquisition of parameter data that is indicative of activation of the therapeutic agent and generation of a parameter display that is indicative of the parameter data. The parameter data may represent the ultrasound energy transmitted into the region of interest for activation of the therapeutic agent. The power level, frequency and beam pattern of the transmitted ultrasound energy are known or can be determined. In addition, parameter data may be derived from ultrasound energy received from the region of interest. Received ultrasound energy is indicative of microbubble destruction and is therefore indicative of activation of the therapeutic agent. The transmitted ultrasound energy may be controlled based on the acquired parameter data and/or the parameter display.

Figure 3:
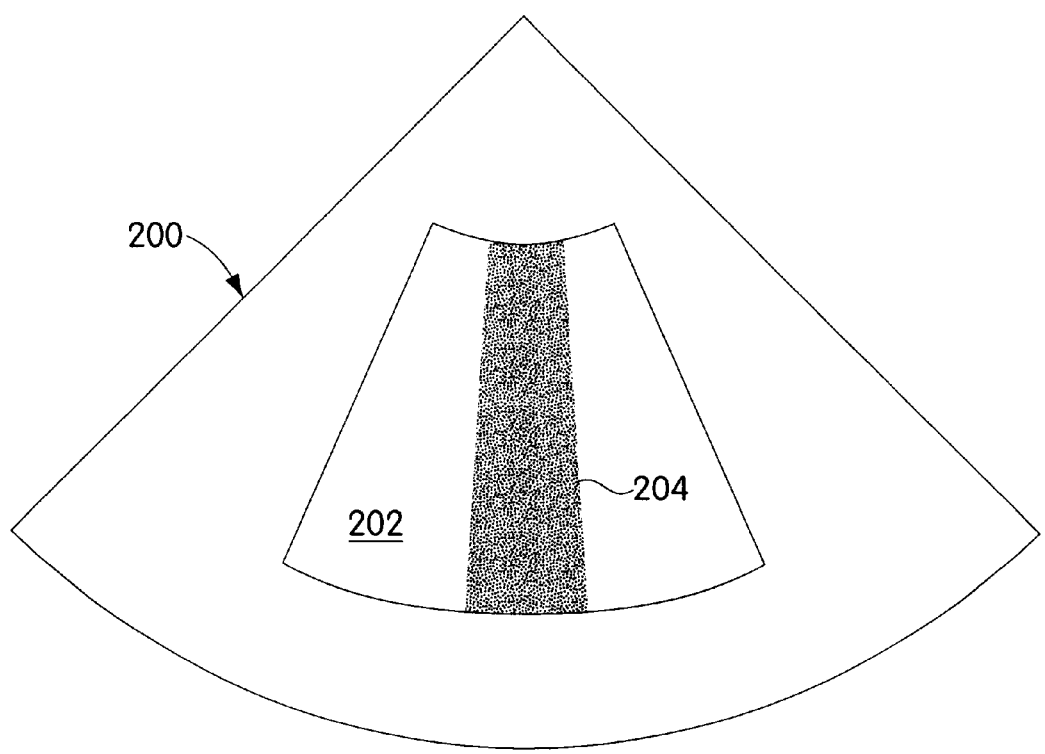
FIG. 3 shows an example of a display screen including an ultrasound image and an overlay that is indicative of activation of a therapeutic agent.
Figure 4:
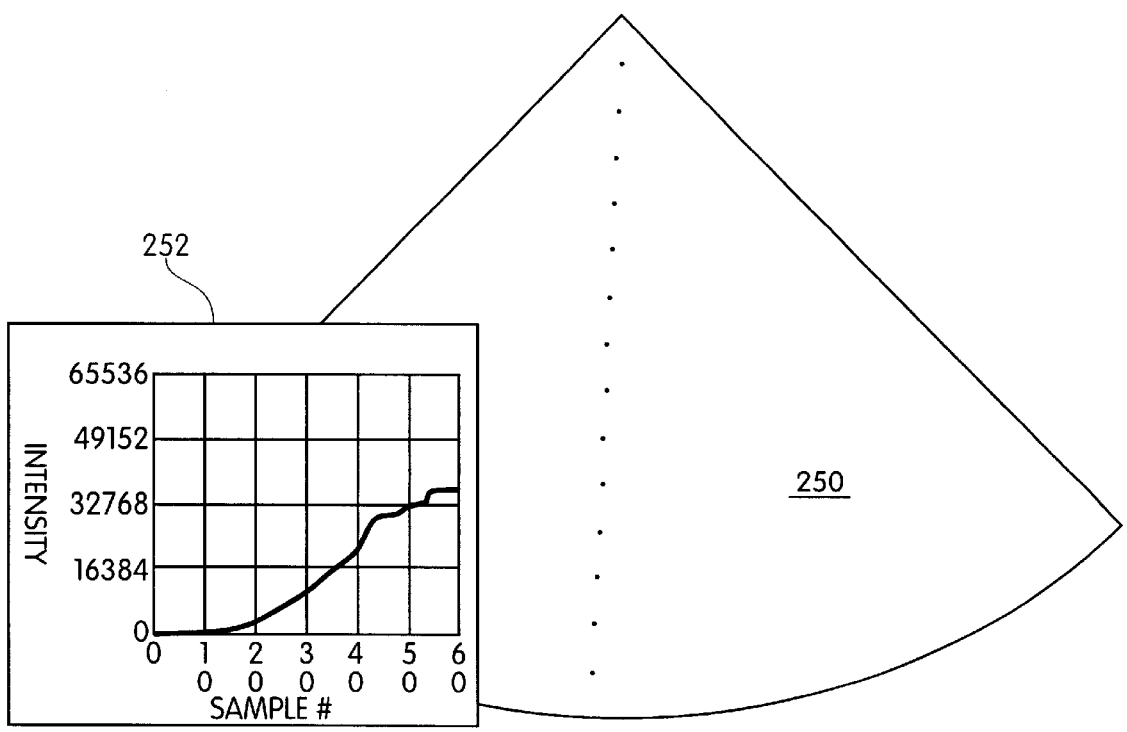
FIG. 4 shows an example of a display screen including an ultrasound image and a graph that is indicative of accumulated dosage of a therapeutic agent.
Figure 5:
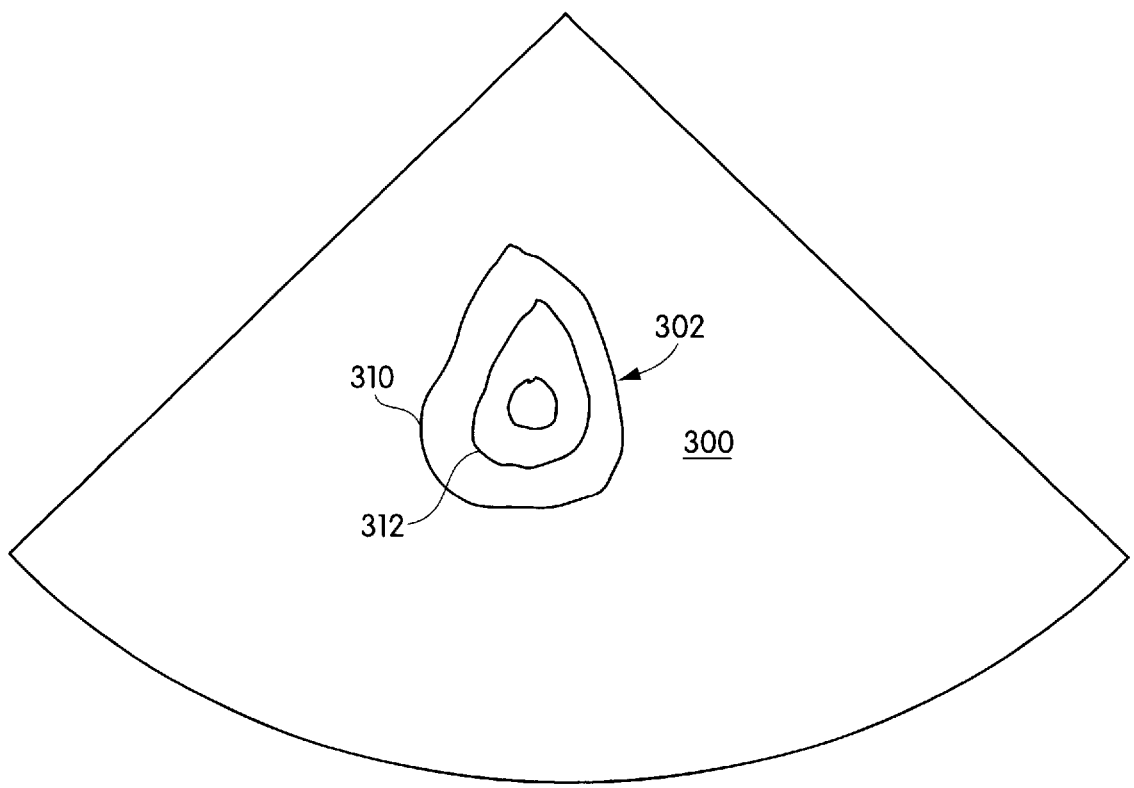
FIG. 5 shows an example of a display screen including an ultrasound image and contours representative of a parameter associated with activation of a therapeutic agent.

Examples of suitable parameter displays are shown in FIGS. 3–5. In FIG. 3, an ultrasound image 200 of the region of interest is generated on the display screen of video display unit 30 in conventional fashion. Image 200 is a sector scan image. A colorized parameter display 202 is superimposed on image 200 as an overlay. In the colorized parameter display 202, different colors represent different values or ranges of values of a parameter that is indicative of activation of the therapeutic agent. As described above, the parameter represented by colorized display 202 may be a parameter of the transmitted ultrasound energy, a parameter of the received ultrasound energy, or both. Thus, for example, a region 204 of colorized display 202 having a specified color may represent a parameter value or range of values of the transmitted ultrasound energy, such as maximum power, or a parameter value or range of values of the received ultrasound energy, such as maximum microbubble destruction. In another example, colorized display 202 represents the cumulative dose of the therapeutic agent delivered to the region of interest. The colorized display 202 shows the spatial distribution of the parameter being displayed.

Referring to FIG. 4, the display screen of video display unit 30 may include a sector scan ultrasound image 250 and a graphic parameter display 252. The graphic parameter display 252 may partially overlay ultrasound image 250 or may be separated from image 250. Graphic parameter display 252 may plot a parameter that is indicative of activation of the therapeutic agent in a defined region of interest as a function of time or as a function of a spatial parameter. In one example, cumulative dose of the activated therapeutic agent is plotted as a function of time.

Referring to FIG. 5, the display screen of the video display unit 30 may include a sector scan ultrasound image 300 and a contour parameter display 302 that overlays ultrasound image 300. The contour parameter display 302 may include contours 310, 312, etc. of constant value of a parameter that is indicative of activation of the therapeutic agent. For example, contours 310, 312, etc. may represent constant pressure, constant frequency, constant power, constant microbubble destruction, and the like. The contour parameter display 302 shows the spatial distribution of the parameter being displayed.

Various techniques can be utilized to detect microbubble destruction. Backscatter intensity may be detected as an indicator of the presence of contrast agent as a function of time. Bubble destruction creates broad band backscatter, resulting in received energy at frequencies in which there is no transmit energy. This is indicative of bubble destruction. This technique is essentially an application of acoustic densitometry, as described by J. Cheirif in "HP Acoustic Densitometry: A New Echocardiographic Method for the On-Line Quantitative Assessment of Contrast Echocardiograms", Application Note, 1996. Known video densitometry techniques may also be utilized to detect microbubble destruction. Subtraction of successive ultrasound images is another approach to determining the amount of contrast agent that has been destroyed and therefore the amount of therapeutic agent that has been activated. In each case, the measured values may be integrated over time to determine cumulative dose of the therapeutic agent and/or to produce a display of cumulative dose.

Another technique for detecting microbubble destruction involves detection of loss of correlation between scan lines using color Doppler or power Doppler, as described by P. Rafter in "Harmonic Power Doppler Technology", Fourth Heart Centre Symposium on Ultrasound Contrast Imaging, Jan. 21–22, 1999. Integration over time is used to determine cumulative dose of the therapeutic agent.

A variety of different parameters may be indicative of activation of the therapeutic agent. Parameter data can be acquired separately or in combination and may or may not be processed to provide a parameter display that is indicative of activation of the therapeutic agent. The parameter display can have a variety of different formats within the scope of the present invention. As indicated above, the parameter display can be an overlay on the ultrasound image or can be a separate display. The parameter display and the ultrasound image can be presented on the same display screen or on separate display screens. The parameter display can be used as an aid in investigating delivery of the therapeutic agent. For example, an investigator may wish to study the effect of a parameter change upon activation of the therapeutic agent by observing the parameter display when the parameter is changed. Alternatively, or in addition to investigation, the parameter display may be used to provide feedback for interactive control of the activation process. Thus, when the parameter display shows a deviation from a desired dose or spatial distribution of the therapeutic agent, the parameters of the transmitted ultrasound energy, such as power level, beam pattern, frequency, and the like, can be adjusted, or application of ultrasound energy can be terminated. The control of the transmitted ultrasound energy can be manual or automatic.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for administering a therapeutic agent to a patient, comprising the steps of:
   delivering a therapeutic agent to a region of interest in a patient;
   generating an ultrasound image of the region of interest at a first ultrasound frequency selected for image quality;
   transmitting ultrasound energy at a second ultrasound frequency that is not equal to the first ultrasound frequency,
   said second ultrasound frequency being transmitted to the region of interest for activating the therapeutic agent; and
   generating a parameter display including an amount of microbubble destruction in the defined region of interest that is indicative of activation of the therapeutic agent in the region of interest and provides feedback control for said activating step; and
   automatically adjusting a parameter related to the second ultrasound frequency in accordance with feedback control, wherein said parameter to be adjusted includes one of frequency, power level, beam pattern, or duration of the transmission of the ultrasound energy.

2. A method for administering a therapeutic agent as defined in claim 1 wherein the step of generating a parameter display comprises generating a display that represents a parameter of the ultrasound energy transmitted to the region of interest.

3. A method for administering a therapeutic agent as defined in claim 1 wherein the step of generating a parameter display comprises generating a colorized display in which specified colors are indicative of parameter values or ranges of values associated with activating the therapeutic agent.

4. A method for administering a therapeutic agent as defined in claim 1 wherein the step of generating a parameter display comprises generating a colorized display in which specified colors are indicative of cumulative dose of the therapeutic agent activated in the region of interest.

5. A method for administering a therapeutic agent as defined in claim 1 wherein the step of generating a parameter display comprises detecting cumulative dose of the therapeutic agent activated in the region of interest and generating a display that is indicative of the cumulative dose.

6. A method for administering a therapeutic agent as defined in claim 1 wherein the step of generating a parameter display comprises generating a graphical representation of a parameter associated with activation of the therapeutic agent.

7. A method for administering a therapeutic agent as defined in claim 1 wherein the step of delivering a therapeutic agent comprises delivering the therapeutic agent incorporated into microbubbles of a contrast agent and wherein the step of transmitting ultrasound energy comprises destroying the microbubbles of the contrast agent for activating the therapeutic agent.

8. A method for administering a therapeutic agent as defined in claim 7 wherein the step of generating a parameter display comprises detecting destruction of microbubbles of the contrast agent and generating a display that is indicative of destruction of microbubbles of the contrast agent.

9. A method for administering a therapeutic agent as defined in claim 8 wherein the step of detecting destruction of microbubbles of the contrast agent comprises detecting loss of correlation between scan lines in said ultrasound image.

10. A method for administering a therapeutic agent as defined in claim 8 wherein the step of detecting destruction of microbubbles of the contrast agent comprises detecting microbubble destruction by acoustic densitometry.

11. A method for administering a therapeutic agent as defined in claim 8 wherein the step of detecting destruction of microbubbles of the contrast agent comprises detecting microbubble destruction by video densitometry.

12. A method for administering a therapeutic agent as defined in claim 8 wherein the step of detecting destruction of microbubbles of the contrast agent comprises detecting microbubble destruction by subtracting successive ultrasound images of the region of interest.

13. A method for administering a therapeutic agent as defined in claim 8 further comprising the step of automatically adjusting one or more parameters of the ultrasound energy transmitted to the region of interest, based on acquired parameter data.

14. A method for administering a therapeutic agent as defined in claim 1 further comprising the step of manually adjusting one or more parameters of the ultrasound energy transmitted to the region of interest, based on said parameter display.

15. A method for administering a therapeutic agent as defined in claim 1 wherein the step of generating a parameter display comprises detecting the spatial distribution of therapeutic agent activated in the region of interest and generating a display that is indicative of the spatial distribution.

16. A method for administering a therapeutic agent to a patient, comprising the steps of:
delivering a therapeutic agent to a region of interest in a patient;
generating an ultrasound image of the region of interest at a first ultrasound frequency selected for image quality;
transmitting ultrasound energy to the region of interest at a second ultrasound frequency that is not equal to the first ultrasound frequency, said second ultrasound frequency being transmitted for activating the therapeutic agent; and
generating a parameter display including an amount of microbubble destruction in the defined region of interest that is indicative of activation of the therapeutic agent in the region of interest and provides feedback control for said transmitting step; and
automatically adjusting a parameter related to the second ultrasound frequency in accordance with feedback control,
wherein said parameter to be adjusted includes one of frequency, power level, beam pattern, or duration of the transmission of the ultrasound energy, and
wherein the step of generating a parameter display comprises generating an area display that overlays said ultrasound image and is indicative of the spatial distribution of a parameter.

17. A method for administering a therapeutic agent as defined in claim 16 wherein the area display comprises contours of constant value of the parameter.

18. A method for administering a therapeutic agent to a patient, comprising the steps of:
delivering a therapeutic agent to a region of interest in a patient;
generating an ultrasound image of the region of interest at a first ultrasound frequency selected for image quality;
transmitting ultrasound energy at a second ultrasound frequency that is not equal to the first ultrasound frequency, said second ultrasound frequency being transmitted to the region of interest for activating the therapeutic agent; and
generating a parameter display including an amount of microbubble destruction in the defined region of interest that is indicative of activation of the therapeutic agent in the region of interest and provides feedback control for said transmitting step; and
automatically adjusting a parameter related to the second ultrasound frequency in accordance with feedback control, wherein said parameter to be adjusted includes one of frequency, power level, beam pattern, or duration of the transmission of the ultrasound energy;
wherein the step of generating a parameter display comprises generating a graphical representation of a parameter associated with activation of the therapeutic agent; and
wherein said graphical representation comprises a graph of cumulative dose of the therapeutic agent as a function of time.

19. Apparatus for facilitating administration of a therapeutic agent to a patient, wherein the therapeutic agent is incorporated into microbubbles of a contrast agent and is delivered with the contrast agent to a region of interest in the patient, comprising:

means for generating an ultrasound image of the region of interest at a first ultrasound frequency selected for image quality;
means for transmitting ultrasound energy to the region of interest at a second ultrasound frequency that is not equal to the first ultrasound frequency and having a different power level, said second ultrasound frequency being transmitted for destroying the microbubbles of the contrast agent;
means for acquiring parameter data that is representative of destruction of the microbubbles of the contrast agent and provides feedback control for said means for transmitting;
means for generating a parameter display of the acquired parameter data, wherein the parameter display includes an amount of microbubble destruction in the region of interest that is indicative of activation of the therapeutic agent in the region of interest; and
means for automatically adjusting a parameter related to the second ultrasound frequency in accordance with feedback control, wherein said parameter to be adjusted includes one of frequency, power level, beam pattern, or duration of the transmission of the ultrasound energy.

20. Apparatus as defined in claim 19 wherein said means for generating a parameter display comprises means for generating a display that represents a parameter of the ultrasound energy transmitted to the region of interest.

21. Apparatus as defined in claim 19 wherein said means for generating a parameter display comprises means for detecting destruction of microbubbles of the contrast agent and generating a parameter display that is indicative of destruction of microbubbles of the contrast agent.

22. Apparatus as defined in claim 19 further comprising means for manually adjusting one or more parameters of the ultrasound energy transmitted to the region of interest, based on said parameter display.

23. Apparatus as defined in claim 19 further comprising means for automatically adjusting one or more parameters of the ultrasound energy transmitted to the region of interest, based on acquired parameter data.

24. Apparatus as defined in claim 19 wherein said means for generating a parameter display comprises means for generating a colorized display in which specified colors are indicative of cumulative dose of the therapeutic agent activated in the region of interest.

25. Apparatus as defined in claim 19 wherein said means for generating a parameter display comprises means for generating a colorized display in which specified colors are indicative of parameter values or ranges of values associated with activating the therapeutic agent.

26. The apparatus as defined in claim 19, wherein said means for generating a parameter display comprises means for generating an area display that overlays said ultrasound image and is indicative of the spatial distribution of a parameter.

27. The apparatus as defined in claim 26, wherein the area display comprises contours of constant values of the parameter.

28. The apparatus as defined in claim 19, wherein said means for generating a parameter display comprises generating a graphical representation of a parameter associated with activation of the therapeutic agent, wherein the graphical representation comprises a graph of the cumulative dose of the therapeutic agent as a function of time.

29. A method for administering a therapeutic agent to a patient, comprising the steps of:

delivering to a region of interest in a patient a therapeutic agent that is incorporated into microbubbles of a contrast agent;

generating an ultrasound image of the region of interest at a first ultrasound frequency selected for image quality;

transmitting ultrasound energy to the region of interest at a second ultrasound frequency that is not equal to the first ultrasound frequency, said second ultrasound frequency being transmitted for destroying the microbubbles of the contrast agent;

acquiring parameter data including an amount of microbubble destruction in the region of interest that is indicative of activation of the therapeutic agent in the region of interest and provides feedback control for said transmitting step; and automatically adjusting one or more parameters of the ultrasound energy transmitted to the region of interest, based on the feedback control, wherein said parameter to be adjusted includes one of frequency, power level, beam pattern, or duration of the transmission of the ultrasound energy.

30. The method according to claim 29, further comprising display the acquired parameter data in an area display that overlays said ultrasound image and is indicative of the spatial distribution of a parameter of said parameter data.

31. The method according to claim 30, wherein the area display comprises contours of constant value of the parameter.

32. The method according to claim 29, further comprising:

displaying a parameter associated with activation of the therapeutic agent in a graphical representation comprising a graph of a cumulative dose of the therapeutic agent as a function of time.

* * * * *